United States Patent [19]
Johannessen et al.

[11] Patent Number: 5,565,650
[45] Date of Patent: Oct. 15, 1996

[54] NON-DETONABLE POLY(GLYCIDYL AZIDE) PRODUCT

[75] Inventors: Birger Johannessen, Maplewood; Anthony P. Manzara, Lake Elmo, both of Minn.

[73] Assignee: Minnesota Mining and Manufacturing Company, St. Paul, Minn.

[21] Appl. No.: 187,323

[22] Filed: Dec. 3, 1993

Related U.S. Application Data

[63] Continuation of Ser. No. 528,866, May 25, 1990, abandoned.

[51] Int. Cl.⁶ .................................................. C06B 45/10
[52] U.S. Cl. ............................................. 149/19.6; 552/11
[58] Field of Search ...................... 149/19.6; 552/10–12

[56] References Cited

U.S. PATENT DOCUMENTS

| | | | |
|---|---|---|---|
| 4,393,199 | 7/1983 | Manser | 149/19.6 |
| 4,483,978 | 11/1984 | Manser | 149/19.6 |
| 4,879,419 | 11/1989 | Johannessen | 568/606 |
| 4,919,737 | 4/1990 | Biddle et al. | 149/19.6 |
| 4,938,812 | 7/1990 | Flanagan et al. | 149/19.6 |
| 4,938,814 | 7/1990 | Schöyer et al. | 149/19.9 |
| 4,962,213 | 10/1990 | Frankel et al. | 552/12 |
| 5,124,463 | 6/1992 | Ampleman | 552/11 |

FOREIGN PATENT DOCUMENTS

| | | |
|---|---|---|
| 0293555 | 12/1988 | European Pat. Off. . |
| 0296310 | 12/1988 | European Pat. Off. . |
| 2285624 | 7/1995 | United Kingdom . |

*Primary Examiner*—Edward A. Miller
*Attorney, Agent, or Firm*—Gary L. Griswold; Walter N. Kirn; Eloise J. Maki

[57] ABSTRACT

A normally liquid, non-detonable product having less than about 45.7 weight percent nitrogen comprising polymer which can be represented by the general formula:

$$R(G)_n R^1$$

where, in the above formula, n is a number between 2 and 18;

G is an azidomethyloxyethylene moiety;

R is a monovalent residue of an organic initiator compound or a monovalent alkyl radical, R is essentially free of isocyanate-reactive moieties and may be substituted with non-interfering atoms or moieties and it cannot be substituted with energetic nitrogen-containing moieties other than azido moieties;

$R^1$ is a monovalent alkoxy radical, oxyaryl radical or combinations thereof, or $R^1$ is an azido moiety, $R^1$ is essentially free of isocyanate-reactive atoms or moieties and it may be substituted with non-interferring atoms or moieties and it cannot be substituted with energetic nitrogen-containing moieties other than azido moieties; or R and $R^1$, taken together, are a carbon-oxygen bond when said polymer is a cyclic compound.

8 Claims, No Drawings

NON-DETONABLE POLY(GLYCIDYL AZIDE) PRODUCT

This is a continuation of application No. 07/528,866, filed May 25, 1990, and now abandoned.

Solid rocket or gun propellants, gas generating compositions or explosives can be prepared by combining various solid and liquid ingredients with a liquid binder polymer to form a pourable liquid slurry of the propellant ingredients. The liquid slurry can then be formed into a solid propellant by placing the slurry in a mold, and curing the liquid binder polymer to an elastomeric form. Typically, plasticizers are used in solid propellant compositions to improve the processibility of the liquid slurry and to improve the mechanical properties of the cured propellant. Preferably, plasticizers are energetic materials and do not contain moieties which are reactive and can interfere with the binder polymer cure. Useful plasticizers should also be compatible, that is, miscible and nonreactive, with the components of the solid propellant formulation.

One useful class of liquid binder polymers are poly(azidomethyloxyethylene) polymers (also known as poly(glycidyl azide) polymers) having terminal hydroxyl moieties. Such polymers can be cured by reacting the hydroxyl moieties with polyisocyanates.

Unfortunately, many of the energetic plasticizers described in the art or currently in use which are compatible with such poly(glycidyl azide) binder polymers are detonable, that is, they would be classified as "Class A Explosive" materials under 37 C.F.R. §173.53. For example, nitrate esters such as nitroglycerin and trimethylolethane trinitrate have been used as energetic plasticizers in solid propellant formulations containing hydroxyl-moiety-terminated poly(glycidyl azide) binder polymer, but both materials are Class A explosives. Extra precaution must be used during the manufacture, transportation and storage of Class A explosive materials. The extra precaution generally results in greater manufacturing, transportation and storage expense.

Thus, there is a need for an energetic, nondetonable material which is compatible with liquid binder polymers, particularly those binder polymers which are cured by reacting with polyisocyanates, and which is useful as a plasticizer.

U.S. Pat. No. 4,781,861 (Wilson et al.) describes certain poly(glycidyl azide) polymers made by reacting polyepichlorohydrin-nitrates of the general formula

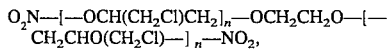
O₂N—[—OCH(CH₂Cl)CH₂]ₙ—OCH₂CH₂O—[—CH₂CHO(CH₂Cl)—]ₙ—NO₂, where n is 1 to 10, with sodium azide in a polar solvent. While the Wilson et al patent states that such poly(glycidyl azide) polymers are useful as energetic plasticizers, and some of the described polymers may contain less than 45.7 percent nitrogen, the patent does not disclose Applicants' non-detonable product.

This invention provides, in one aspect, a normally liquid, non-detonable, energetic product having less than about 45.7 weight percent nitrogen comprising polymer which can be represented by the general formula:

R(G)ₙR¹     I where, in the above formula,
n is a number between 2 and 18;
G is an azidomethyloxyethylene moiety [—OCH(CH₂N₃)CH₂—] or [—OCH₂CH(CH₂N₃)—]; and R is a monovalent residue of an organic initiator compound (such as the residue of a straight chain, branched or cyclic aliphatic or aromatic alcohol (e.g., —CH₂CH₂N₃ and —CH₂CH₂CH₂N₃), preferably having between one and ten carbon atoms), or R can be a monovalent straight chain, branched or cyclic alkyl radical (e.g., —CH₃, —CH₂CH₃, —CH₂CH₂CH₃, —CH₂CN₂N₃ and CH₂CH₂ CH₂N₃), R is essentially free of isocyanate-reactive moieties (such as moieties containing active hydrogen atoms), and may be substituted with non-interfering atoms or moieties (e.g., fluorine atoms, azido moieties and cyano moieties) and it cannot be substituted with energetic nitrogen-containing moieties other than azido moieties;

R¹ is a monovalent, alkoxy radical which can be straight chain, branched or cyclic, or R¹ can be a monovalent oxyaryl radical, or combinations thereof (e.g., monovalent oxyalkaryl or oxyaralkyl radicals), or R¹ is an azido moiety, R¹ is essentially free of isocyanate-reactive moieties, and it may be substituted with non-interfering atoms or moieties (e.g., fluorine atoms, azido moieties and cyano moieties) and it cannot be substituted with energetic nitrogen-containing moieties other than azido moieties, and representative examples of R¹ include —OCH₃, —OCH₂CH₃, —OCH₂CH₂CH₃ and —OCH₂C₆H₅; or R and R¹, taken together, are a carbon-oxygen bond when said polymer is a cyclic compound.

In order to determine whether a product is detonable, 120 grams of the product is thoroughly mixed with 8 grams of cotton in a plastic cup approximately two inches in diameter and four inches high and the cup is placed on top of a lead witness cylinder about four inches (10.2 cm) high and 1.25 inches (3.2 cm) in diameter. A blasting cap is inserted into the cotton and is positioned approximately in the center of the cup. The blasting cap is detonated electrically and the resulting reaction is observed. The product is considered detonable if a loud report and a fireball are observed and the witness cylinder is deformed (e.g., shortened or mushroomed) such that it decreased more than one eighth of an inch (0.32 cm) from its original height.

The product of this invention is normally liquid. Generally, substantially or essentially all of the nitrogen in the product is present in the form of azido moieties. The product must contain sufficient azido moieties to be energetic, e.g., preferably containing at least 30 weight percent nitrogen, but not enough of the moieties to make the product detonable, that is, not more than about 46 weight percent nitrogen. The presence of too many azidomethyloxyethylene moieties (hereinafter, for brevity, occasionally referred to as glycidyl azide moieties) in the product can result in a product which is too viscous to be very useful as a plasticizer. Typically, the product can have a number average molecular weight, for example, of about 200 to 2000, and preferably of about 400 to 1000. Generally, if the product has a molecular weight below 200 it is less desirable for use as a plasticizer because of its high volatility. The azidomethyloxyethylene moieties making up the major portion of the product by weight are generally present in the form of homopolymer chains (i.e., —[OCH₂CH(CH₂N₃)]ₙ— or —[OCH₂CH(CH₂N₃)CH₂]ₙ—, where n is a number from 2 to 18). Typically, at least 50 weight percent of the product, and preferably at least 70 weight percent of the product, comprises such homopolymer chains. The product contains less than about 45.7 weight percent nitrogen, and preferably no more than about 44 weight percent nitrogen, and at least 30 weight percent nitrogen in the form of azido moieties.

The product of this invention is also essentially free of isocyanate-reactive moieties such as moieties having active hydrogen atoms (i.e., hydrogen atoms which will react with isocyanate moieties under urethane bond forming conditions). Generally, such hydrogen atoms are those bonded to oxygen, sulfur or nitrogen atoms. The presence of isocyanate-reactive moieties in the product is to be avoided because they can interfere with the cure of isocyanate-reactive binder polymer such as hydroxyl-terminated poly(glycidyl azide) binder polymer. Preferably, the product will contain no more than about one equivalent of isocyanate-reactive moieties in each 30,000 grams of product.

The product of this invention is also essentially free of, and preferably contains no, energetic nitrogen-containing moieties other than azido moieties. This is because the presence of such moieties in the product can increase the detonability of the product. Representative examples of energetic, nitrogen-containing moieties not included in the product are nitrate esters, trinitromethyl, fluorodinitromethyl, dinitromethylene and nitraza moieties.

Representative examples of poly(glycidyl azide) polymers which may comprise the product of this invention include $CH_3OCH_2CH(CH_3)OCH_2CH(CH_3)$ $[(OCH_2CH(CH_2N_3)]_n$, $N_3$, $CH_3CH_2[OCH_2CH(CH_2N_3)]_n$ $OCH_2CH_3$, $N_3CH_2CH_2[$ $OCH_2CH(CH_2N_3)]_nN_3$, $CH_3OCH_2CH_2[OCH_2CH(CH_2N_3)]_nN_3$, and $CH_3O$ $[CH_2CH(CH_2\ N_3)]_nN_3$
where n is a number between 2 and 18, and preferably between 4 and 11.

The products of this invention can be prepared by reacting azide salts with polyepichlorohydrin polymer. Typically, inorganic azides such as potassium azide, lithium azide and sodium azide are used to prepare the product. Generally, sodium azide is the preferred inorganic azide. The product is prepared by reacting the polyepichlorohydrin polymer in the conventional manner with the inorganic azide, such as sodium azide. The reaction results in the displacement of halide atoms, generally chlorine, or other displacable groups, such as sulfonate ester groups, by azide ion (i.e. $N_3^-$). Detailed descriptions of procedures which can be used to displace halide atoms or other displacable groups by azide ion are set forth in U.S. Pat. No. 4,268,450 (Frankel et al), U.S. Pat. No. 4,288,262 (Flanagan), U.S. Pat. No. 4,379,894 (Frankel et al), and U.S. Pat. No. 4,486,351 (Earl), which descriptions are hereby incorporated by reference.

One class of polyepichlorohydrin polymer which can be used to prepare the product of this invention includes polymer which can be represented by the following formula:

$$R^3(E)_nR^4 \qquad \qquad II$$

where, in the above formula,
n is as defined above;
E is a chloromethylethyleneoxy moiety, ($-OCH_2CH(CH_2Cl)-$) or ($-OCH(CH_2Cl)CH_2-$), hereinafter, for brevity, occasionally referred to as an epichlorohydrin moiety;
$R^3$ is a monovalent residue of an organic initiator compound (such as the residue of a straight chain, branched or cyclic aliphatic or aromatic alcohol, preferably having between one and ten carbon atoms), or a monovalent straight chain, branched or cyclic alkyl radical (e.g., $-CH_3$, $-CH_2CH_3$, $-CH_2CH_2CH_3$, $-CH_2CH_2Cl$), $R^3$ is essentially free of isocyanate-reactive moieties, may be substituted with non-interfering atoms or moieties (e.g., fluorine atoms and cyano moieties) but cannot be substituted with energetic nitrogen-containing moieties; and
$R^4$ is a monovalent, alkoxy radical which may be straight chain, branched or cyclic, or a monovalent oxyacyl radical, or combinations thereof, or $R^4$ is a displaceable group such as a sulfonate ester group (e.g., $-OSO_2C_6H_5$, $-OSO_2CH_3$, $-OSO_2C_6H_4CH_3$ and $-OSO_2CF_3$) or a halogen atom, $R^4$ is essentially free of isocyanate-reactive moieties and may be substituted with non-interfering atoms or moieties (e.g., fluorine atoms and cyano moieties) but cannot be substituted with energetic nitrogen-containing moieties other than azido moieties and examples of $R^4$ include $-OCH_3$, $-OCH_2CH_3$ and $-OCH_2CH_2CH_3$, $-OCH_2CH_2Cl$ and $-OCH_2C_6H_5$; or
$R^3$ and $R^4$, taken together, are a carbon-oxygen bond when said polyepichlorohydrin is a cyclic compound.

Polyepichlorohydrin polymer can be prepared in a number of ways by polymerization of epichlorohydrin. One method of preparing cyclic polyepichlorohydrin polymer includes the polymerization of epichlorohydrin in the presence of an acid catalyst using the method described in Kern, R. J., *Journal of Organic Chemistry*, 33, (1960) pp. 388–390 (which description is herein incorporated by reference). In this method, epichlorohydrin dissolved or dispersed in a suitable solvent, such as carbon tetrachloride, is polymerized in the presence of known epichlorohydrin polymerization catalysts such as Lewis acid catalysts, e.g., $(C_2H_5)_3OBF_3$ or $BF_3$. Also useful in this method are catalysts which can be represented by the following general formula:

$$HN(R^wSO_2)_2 \qquad \qquad III$$

$$HCR^5(R^wSO_2)_2 \qquad \qquad IV$$

$$HC(R^wSO_2)_3 \qquad \qquad V$$

where, in the above formulas:
$R^w$ is an electron-withdrawing moiety, such as a perfluoroalkyl radical having about one to twenty carbon atoms; and
$R^5$ is a non-interfering moiety (ie., a moiety which does not interfere with the epichlorohydrin polymerization), such as aliphatic or aromatic radicals, or a hydrogen atom; and
Optionally, any two ($R^wSO_2$) groups may, taken together, form a cyclic structure, such as $-SO_2CF_2CF_2CF_2CF_2-SO_2-$. Some of these catalysts are described in U.S. Pat. No. 3,776,960 (Koshar et al.), U.S. Pat. No. 4,031,036 (Koshar), U.S. Pat. No. 4,387,222 (Koshar), U.S. Pat. No. 4,405,497 (Young et al), which description is herein incorporated by reference.

A method of preparing non-cyclic polyepichlorohydrin polymer involves the insertion of two or more moieties, derived from epichlorohydrin, into an ether molecule. The reaction takes place in the presence of a Lewis acid catalyst using the general procedure of described in U.S. Pat. No. 4,146,736 (Scheffel et al.) (which description is herein incorporated by reference). Ether molecules useful for preparing the polyepichlorohydrin polymer can be represented by the general formula $$R^6R^7 \qquad \qquad VI$$

where, in the above formula,
$R^6$ is a monovalent, straight chain, branched or cyclic aliphatic radical, having 1 to 10 carbon atoms and preferably 1 to 4 carbon atoms; and
$R^7$ is a monovalent, straight chain, branched or cyclic alkoxy radical, having 1 to 10 and preferably 1 to 4 carbon atoms.

Representative ethers useful in this invention which can be represented by the formula VI include dimethyl ether, diethyl ether, di-butyl ether, methyl ethyl ether, methyl propyl ether, chloro-methyl propyl ether, methyl butyl ether, and bis 3-chloropropyl ether. Representative catalysts useful in this process include metal halides and metalloid halides (e.g., $BF_3$, $FeCl_3$, $SnCl_4$ and $PF_3$), hydrogen acids (e.g., HF), aluminum hydrosilicates (e.g., montmorillonite), coordination complexes of metal halides or metalloid halides with organic compounds such as halogenoalkyls, ethers, acid chlorides, acid esters or acid anhydrides, trialkyloxonium salt complexes having identical or different alkyl groups, analogous acylium salt complexes, and unsaturated tertiary oxonium salts. Preferably, the epichlorohydrin polymerization catalysts depicted by formulas III, IV and V are used in this method. Where stannic chloride is used, it is preferable that the reactants used in the preparation of the polyepichlorohydrin polymer be in substantially anhydrous condition.

Another method of preparing non-cyclic polyepichlorohydrin polymer involves the polymerization of epichlorohydrin molecules in the presence of an alcohol initiator and known epichlorohydrin polymerization catalyst or the epichlorohydrin polymerization catalyst depicted in formulas III, IV and V. The resulting hydroxyl-functional polyepichlorohydrin polymer (i.e., polyepichlorohydrin polymer having one or more hydroxyl moieties) is then reacted with an alkylating or esterifying agent such that the resulting polyepichlorohydrin polymer has essentially no hydroxyl moieties. Alternatively, the hydroxyl-functional polyepichlorohydrin polymer can be first reacted with ionic azide as described above, and the resulting hydroxyl-functional poly(glycidyl azide) polymer can then be reacted with the alkylating agent (e.g., dimethyl sulfate or methyl iodide) to provide the product of this invention.

Some of the epichlorohydrin polymerization catalysts useful in this last method are known and include triethyloxonium hexafluorophosphate, boron trifluoride etherate, or the combination of a fluorinated acid and a polyvalent organotin compound, e.g., diphenyldibutyltin, as described in U.S. Pat. No. 4,431,845. Also useful in this process is the novel catalyst $C_6H_5$—$CH(SO_2CF_3)_2$. However, preferably anhydrous stannic chloride per se or in combination with a strong carboxylic acid (i.e., one having a $pK_a$ of less than about 2, preferably less than about 1) such as trifluoroacetic acid or trichloroacetic acid is used (for example, see U.S. Pat. No. 4,879,419). The initiators which may be used in this method are unreactive with the polymerization catalyst (e.g., stannic chloride) and are monohydric compounds. Representative illustrative initiators which can be used include monohydric aliphatic alcohols, such as $CH_3OH$, $C_2H_5OH$, $(CH_3)_2CHOH$, $CH_3(CH_2)_3OH$, $ClC_2H_4OH$, and $CH_3(CH_2)_{16}CH_2OH$, monohydric cycloaliphatic alcohols, such as $C_6H_{11}CH_2OH$, phenols and aromatic alcohols. Mixtures of such initiators can also be used.

When used to prepare polyepichlorohydrin polymer, the amount of stannic chloride catalyst to be used without the co-catalyst in preparing the polyepichlorohydrin polymer is that amount sufficient to result in generally substantially quantitative or preferably essentially complete conversion of the epichlorohydrin to the polyepichlorohydrin polymer and the amount of stannic chloride to be used will depend on the desired molecular weight of the polyepichlorohydrin polymer. Generally, for a product having a desired molecular weight of about 2000, the amount of stannic chloride will be about 0.5 to 1 weight percent of the polymerization reaction mixture; and for a product with a molecular weight of about 1000, such amount will be about 0.25 to 0.5 weight percent.

Where a strong carboxylic acid is used as a co-catalyst in preparation of the polyepichlorohydrin polymer, generally, the strong carboxylic acid co-catalysts used are those having a $pK_a$ of less than 2 and preferably less than 1, as determined, for example, by the method described by W. Huber, "Titration in Nonaqueous Solvents," Academic Press, New York, N.Y., 1967, p 215. A class of such acid co-catalysts can be represented by the formula R'—CXY—COOH, where X and Y are independently selected from the group consisting of chlorine and fluorine, and R' is hydrogen, fluorine, chlorine, or a moiety which is electron-withdrawing (relative to hydrogen), e.g., —$C_2F_5$ and —$C_6H_5$, and does not adversely affect the polymerization. Representative co-catalysts (and their $pK_a$ values) include trifluoroacetic acid (0.234), trichloroacetic acid (0.66), and dichloroacetic acid (1.25).

Generally, the molar ratio of stannic chloride to co-catalyst will be 1:0.5 to 1:1.0, preferably 1:3 to 1:5, higher amounts of the co-catalyst in these ranges acting significantly as an initiator and thus influencing the molecular weight of the polyepichlorohydrin polymer.

The epichlorohydrin polymerization can be carried out in the presence of a solvent or inert diluent. Suitable solvents representatively include 1,2-dichloroethane, benzene, toluene, methylene chloride, and carbon tetrachloride. The catalyst(s) can be added to the reaction vessel containing the initiator and solvent and the epichlorohydrin can be then incrementally added. Prior to adding the epichlorohydrin, and during its addition and the ensuing reaction, the reaction vessel is heated or cooled to a desired polymerization temperature, e.g., about 0° C. to 110° C., preferably 65° C. to 75° C. The polymerization reaction is conducted under anhydrous conditions and to that end a slow, dry nitrogen gas purge of the reaction vessel can be used. The reaction pressure is generally the autogeneous pressure but superatmospheric pressures can be used, e.g., up to 10 atmospheres, where the more volatile initiators are used.

The resulting polyepichlorohydrin polymer can be recovered by subjecting the reaction product mixture to reduced pressure to remove solvent and volatile material, e.g., unreacted epichlorohydrin, adding further solvent, and then extracting the non-volatile material with an extracting agent, such as aqueous organic solvent, e.g. alcohol such as methanol, containing ammonium hydroxide, or a chelating agent for tin such as the tetrasodium salt of ethylenedinitrilotetracetic acid (i.e., $EDTANa_4.2H_2O$), used in an amount of about 5 to 10 percent in excess of the equivalent amount necessary to complex with the stannic chloride and neutralize the acid co-catalyst (if present). The resulting two phases are separated, the heavier phase containing the desired polyepichlorohydrin product and the other phase being the aqueous organic solvent containing the chelating agent and catalysts. The product phase can be washed several additional times with aqueous organic solvent. The washed product can be stripped under reduced pressure.

The products of this invention can be mixed with solid particulate oxidizer, binder prepolymers and optionally other fuel components, bonding agents, processing aids, burn rate catalysts, cure catalysts, carbon black and combustion stabilizers to form solid rocket propellants. These propellant ingredients can be blended in a slow speed, high-shear mixer until all the solid particles are wetted by the liquids in the system, the mixing optionally being carried out under vacuum to remove trapped air. A polyisocyanate curing agent is then added. An additional short mixing cycle is completed. The viscous, uncured propellant slurry can be transferred into a prepared rocket motor casing. The filled casing can then be slowly heated to the appropriate cure temperature (generally 55° to 80° C.) and held at that temperature until the urethane reaction has taken place and the liquid binder precursor is converted to a solid, elastomeric polyurethane matrix providing mechanical integrity, environmental protection, and a controlled burning surface to the resulting solid propellant. Such propellants can be used in aircraft starter cartridges and ducted rocket boosters, and, as high energy propellant, low signature propellants, minimum smoke propellant, and gun propellants. The product of this invention is also useful as a plasticizer in explosive compositions or pyrotechnic compositions (i.e., energetic compositions used to produce heat, light or smoke but not force).

Generally, the product of this invention also tends to have a lower freezing point and greater thermal stability than conventional nitrate ester plasticizers, thus providing a plasticizer useful over a greater temperature range than many conventional nitrate ester plasticizers.

Objects and advantages of this invention are illustrated in the following examples.

COMPARATIVE EXAMPLE 1

To a 3 L, 3-necked flask was added 102 g of 2-chloroethanol, 140 g of 1,2-dichloroethane, 7 g of stannic chloride and 14 grams of trichloroacetic acid. The flask was then heated, with stirring, to 70° C. using an electric heating mantle. After reaching 70° C. the heating mantle was removed and 1295 g of epichlorohydrin was added slowly to the contents of the flask. The temperature was maintained at 70° C. by adjusting the addition rate of the epichlorohydrin and by cooling the flask in an ice water bath. The addition of the epichlorohydrin was complete after 2 hours and 25 minutes. The flask was then cooled 30° C. To the cooled reaction mixture was added 200 g of 1,2-dichloroethane followed by a mixture of 7.7 g of sodium hydroxide, 35.7 g of the disodium salt of (ethylenedinitrilo)-tetracetic acid, 250 g of water and 250 g of methanol. The flask was then heated to reflux approximately 65° C.) and stirred for one hour before the contents of the flask were transferred to a 2 L separatory funnel. After separating the phases, the heavier product phase was returned to the reaction flask and the extraction procedure was repeated using a mixture of 250 g water and 250 g methanol. The heavier product phase was again separated using the separatory funnel and residual water and alcohol were stripped from the product for 6 hours using vacuum distillation (maximum temperature 70° C., minimum pressure 5 torr). 1369 g of a 700 molecular weight (MW) monofunctional polyepichlorohydrin polymer were recovered.

To a 2 L, 3-necked flask was added 600 g of the 700 MW monofunctional polyepichlorohydrin polymer, 600 g of 1,2-dichloroethane, and 151 g of benzene sulfonyl chloride. Over a 20 minute period, 69 g of pyridine was added to the mixture in the flask while stirring and maintaining the temperature of the contents of the flask at 20° C. using an ice water bath. The resulting mixture was then cooled to below 10° C. to induce crystallization of pyridine hydrochloride and the resulting mixture was stirred for 6 more hours at 20° C. The mixture was then filtered on a Buchner filter to remove crystalline material and the filtrate was washed by adding 800 g of 1,2-dichloroethane and a solution of 72 g sodium bicarbonate in 1000 g water to the flask. The resulting mixture was stirred for one hour at 20° C. before transferring to a separatory funnel. The mixture in the separatory funnel was allowed stand overnight at room temperature. The product phase was then separated and poured though a 2.5 cm glass column containing 70 g of molecular sieves 4 A (available from Union Carbide Corporation, Linde Division). After passing through the column, the product phase was stripped of solvent by vacuum distillation (maximum temperature 70° C., minimum pressure was 5 torr). After 8 hours of stripping, 638 g of the benzene sulfonyl chloride ester of the monofunctional polyepichlorohydrin polymer was recovered.

To a pint jar, 277 g of the benzene sulfonyl chloride ester of polyepichlorohydrin polymer and 119 g of dimethyl sulfoxide were added and the mixture was gently stirred.

To a 2 L, 3-necked flask, 344 g of dimethyl sulfoxide was added and heated, with stirring, using an electric heating mantle. When the temperature of the dimethyl sulfoxide reached 50° C., 204 g of sodium azide was incrementally added. After adding the sodium azide, the mixture was heated to 90° C. and the mixture of the esterified polyepichlorohydrin and dimethyl sulfoxide was slowly added. The elasped time between the beginning of heating and the time of reaching 90° C. took about 1 hour and 15 minutes. The mixture was stirred at 90° C. for 11 more hours, after which time infrared spectroscopy indicated no more C—Cl absorbance. The product was then washed by adding 833 g of water to the flask. The temperature dropped to 70° C. and the mixture was stirred for 1 hour at this temperature before decanting the aqueous phase and retaining the product phase. The wash procedure was repeated with another 833 g of water. 1,2-Dichlororethane (555 g) was then added to the product phase from the second wash and the mixture was washed with a mixture of 415 g methanol and 415 g of water. A clear product phase was retained after separating from the aqueous phase. The product phase was stripped using vacuum distillation (maximum temperature 55° C., minimum pressure 8 torr). 246 g of the azido derivative

was recovered, wherein n is greater than 1, the average molecular weight of the product was 700 and the average nitrogen content was about 47.6%.

120 grams of the product was thoroughly mixed with 8 grams of cotton in a plastic cup approximately two inches in diameter and four inches high and the cup was placed on top of a lead witness cylinder about four inches high and 1.25 inches in diameter. A blasting cap was inserted into the cotton and positioned approximately in the center of the cup. The blasting cap was then detonated electrically. A loud report was heard and a fireball about 4 feet in diameter was observed. The witness cylinder was re-measured and in two tests found to be shortened by an average of 0.24 inches. This indicates that the product was detonable.

EXAMPLE 1

This example describes the preparation of the poly(glycidyl azide) product comprising polymer having the formula

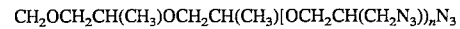

(where n is greater than 1), by preparing monofunctional polyepichlorohydrin polymer having a molecular weight of about 700, esterifying the polymer using benzenesulfonyl chloride and reacting the resulting ester with sodium azide.

To a 3 L, 3-necked flask 296 g of dipropylene glycol monomethyl ether, 140 g of 1,2-dichloroethane, 7 g of stannic chloride, and 14 g of trichloroacetic acid were added.

The flask was heated, with stirring, to 70° C. using an electric heating mantle. After reaching 70° C., the heating mantle was removed and 1104 g of epichlorohydrin was slowly added to the mixture. The temperature of the reaction mixture was maintained at 70° C. by adjusting the addition rate and cooling the flask in an ice water bath. The addition of the epichlorohydrin to the reaction mixture was completed after 2 hours and 10 minutes. The flask was then cooled to 35° C. and a mixture of 40 g of the tetrasodium salt of (ethylenedinitrilo)-tetracetic acid, 250 g water and 250 g methanol was added. The flask was heated to reflux (approximately 65° C.) and stirred for one hour before the content was transferred to a 2 L separatory funnel. After recovering the product phase from the separatory funnel, it was returned to the reaction flask and 250 g of water and 250 g of methanol were added. The mixture was again heated to reflux and stirred for one hour before the content was again transferred to the separatory funnel and the product phase was recovered. Remaining methanol and water were then stripped from the product phase using vacuum distillation. The product phase was stripped for 4 hours (maximum temperature 70° C., minimum pressure 5 torr). After distillation 1335 g of a monofunctional polyepichlorohydrin was recovered.

To a 2 L, 3-necked flask, 600 g of the monofunctional polyepichlorohydrin, 600 g of 1,2-dichloroethane and 237 g of benzene sulfonyl chloride were added. 109 g of pyridine was added to the flask over a 20 minute period while stirring the mixture in the flask and maintaining its temperature at 20° C. using an ice water bath. After addition of the pyridine was completed, the resulting mixture was stirred for two more hours at 20° C. The mixture was then cooled to below 10° C. to induce crystallization of pyridine hydrochloride and the resulting mixture was stirred for 6 more hours at 20° C. The mixture was then filtered on a Buchner filter to remove crystalline material and the filtrate was washed by adding 500 g of 1,2-dichloroethane and a solution of 72 g sodium bicarbonate in 1000 g water to the flask. The resulting mixture was stirred for one hour at 20° C. before transferring the mixture to a separatory funnel. The mixture in the separatory funnel was allowed to stand overnight at room temperature. The product phase was then separated and poured though a 1 inch glass column containing 70 g of molecular sieves 4 A (available from Union Carbide Corporation, Linde Division). After passing through the column, the product phase was stripped of solvent by vacuum distillation (maximum temperature 70° C., minimum pressure was 5 tort). After 8 hours of stripping, 638 g of the benzene sulfonyl chloride ester of the monofunctional poly-epichlorohydrin polymer was recovered.

The azido derivative of the benzene sulfonyl chloride ester of the monofunctional polyepichlorohydrin was prepared according to the procedure similar to that described in Comparative Example 1.

A detonation test was performed on a 120 g sample of the poly(glycidyl azide) product using the procedure described in Comparative Example 1. The material did not explode or ignite but merely scattered around. This indicated that the poly(glycidyl azide) product did not detonate.

EXAMPLE 2

The following example describes the preparation of the poly(glycidyl azide) product comprising polymer represented by the formula

$CH_3CH_2[OCH_2CH(CH_2N_3)]_nOCH_2CH_3$ where n is greater than 2.

Diethylether was reacted with epichlorohydrin using stannic chloride catalyst. This procedure resulted in compounds of various molecular weights where one or more epichlorohydrin units were inserted in the ether. The smallest compound, where n was equal to 1, was removed by vacuum distillation. The residue was then reacted with sodium azide to produce the poly(glycidyl azide) product.

To a 5 L, 3-necked flask 1500 g diethyl ether was added followed by 20 mL stannic chloride and 1000 g epichlorohydrin. The additions were made without delay and were completed in less than 5 minutes. The flask was equipped with an electric heating mantle, a stirrer, thermometer and a condenser. The flask was provided with an inert nitrogen atmosphere above the reaction mixture. The temperature of the reaction mixture rose slowly during the first hour from 26° C. to 39° C. After 5 hours, a sample was taken and gas chromatography showed some unreacted epichlorohydrin so the reaction was allowed to proceed for an additional 19 hours. A sample was again taken from the reaction mixture and gas chromatography indicated that all the epichlorohydrin had reacted. A solution of 110 g of the tetrasodium salt of (ethylenedinitrilo)-tetracetic acid in 1000 g water was added to the reaction mixture. The resulting mixture was stirred for 90 minutes before transferring it to a separatory funnel. After separation of the aqueous phase, a product phase was recovered and added to 100 g of molecular sieves, 3A, available from Union Carbide Corporation, Linde Division. The mixture of product phase and molecular sieves was allowed to rest at room temperature for a two day period. The product phase was then decanted from the molecular sieves and was poured through a 1 inch diameter glass column containing 100 g of the molecular sieves. The product phase was slowly drained from the column through a filter paper into a 3 L, 3-necked flask under a slow nitrogen purge. The product phase was then distilled at atmospheric pressure to recover excess ether. The remaining product phase was then stripped under vacuum to remove volatiles. Ethoxy-terminated polyepichlorohydrin (879 g) was recovered after distillation.

To a 1 L, 3-necked flask equipped with a stirrer, thermometer, temperature controller and condenser was added 200 g of the ethoxy-terminated polyepichlorohydrin and 200 g of dimethylsulfoxide. The resulting mixture was heated with stirring using an electric heating mantle. When the temperature of the mixture reached 50° C., incremental addition of 100 g of sodium azide began. The addition of the sodium azide was completed when the temperature of the mixture in the flask reached 90° C. The reaction mixture was stirred for 30 hours at 90° C. Water (600 g) was then added to the reaction mixture, with stirring, and the mixture was allowed to cool down. The aqueous phase was then decanted from the mixture and discarded and 400 g of water and 400 g of 1,2-dichloroethane were added to the retained phase and the mixture was stirred for 1 hour. The mixture was then transferred to a separatory funnel and the aqueous phase was separated from the product phase. The product phase was then stripped by vacuum distillation (maximum temperature 50° C., minimum pressure 5 torr). Ethoxy-terminated poly(glycidyl azide) product (196 g) was recovered.

A detonation test was performed on a 120 g sample of the poly(glycidyl azide) product according to the procedure described in Comparative Example 1. The material did not explode or detonate, but merely scattered around. This indicates that the poly(glycidyl azide) product did not detonate.

EXAMPLE 3

This example describes the preparation of the poly(glycidyl azide) product comprising polymer having the formula CH₃CH₂[OCH₂CH(CH₂N₃)]ₙOCH₂CH₃, where n is greater than 2 using phenylbis(trifluoromethylsulfonyl)methane as catalyst.

Dried, phenylbis(trifluoromethylsulfonyl)methane (0 023% water) (3.2 g), epichlorohydrin monomer (0.010% water) (1070.0 g) and diethyl ether (0.006% water) (120.0g) were added to a dry 2 L, 3-necked flask. The flask was then stirred and slowly heated to 70° C. This temperature was reached in about 35 minutes. The condenser top was closed and the flask was then stirred, at 70° C., until a total of 24 hours had elapsed. The remaining product was then subjected to two extractions using the following ingredients:

| Ingredients | First extraction | Second extraction |
|---|---|---|
| EDTANa₄.2H₂O | 15 | — |
| Distilled water | 240 | 50 |
| Methanol | 240 | 450 |
| 1,2-Dichloroethane | 360 | — |

Each extraction was stirred for one hour at 65° C. before separating the two phases in a 2 L separatory funnel. The final product phase was stripped for four hours under vacuum to remove the solvents (max. temp. 70° C., min. press. 7 torr). A slow nitrogen purge was also used. After the extractions, 658 g of the epichlorohydrin polymer was recovered.

The polyepichlorohydrin polymer (277 g) was then diluted with 119 g dimethylsulfoxide in a pint jar and heated to 60° C. in an oven. Another 344 g dimethylsulfoxide was added to a 2L, 3-necked flask. A slow nitrogen purge was applied and the flask was heated to 90° C. while stirring. When the temperature reached 50° C., a slow addition of 204 g sodium azide was begun while continuing heating to 90° C. The 60° C. dimethylsulfoxide solution of the polyepichlorohydrin was also added gradually during this period. All additions were completed and 90° C. reached after 75 minutes. The flask was stirred at 90° C. for an additional 19 hours. Infrared spectroscopy indicated the absence of C—Cl bonds.

The poly(glycidyl azide) product was recovered from the reaction mixture after three extractions using the following ingredients:

| Ingredients | Extractions first | second | third |
|---|---|---|---|
| 1,2-Dichloroethane | — | — | 555 |
| Methanol | — | — | 416 |
| Distilled water | 833 | 833 | 416 |

Each extraction was heated to 65° C. and stirred one hour before separating the two phases in a 2 L separatory funnel solvents were vacuum stripped from the final product phase for 4 hours at 60° C. and a minimum pressure of 2 torr. A slow nitrogen purge was also used. The yield was 269 g of the poly(glycidyl azide) product.

Various modifications and alterations of this invention will become apparent to those skilled in the art without departing from the scope and spirit of this invention.

We claim:

1. A normally liquid, non-detonable, energetic poly(glycidyl azide) product having at least 30 weight percent nitrogen in the form of azido moieties yet less than a total of 45.7 weight percent nitrogen and a number average molecular weight of 200 to 2000 that consists essentially of polymer represented by the general formula:

$$R(G)_n R^1$$

where, in the above formula:

n is a number between 2 and 18:

G is (—OCH(CH₂N₃)CH₂—) or (—OCH₂CH(CH₂N₃)—);

R is either a monovalent residue of an organic initiator compound which may be substituted with atoms and moieties selected from the group consisting of hydrogen atoms, chlorine atoms, fluorine atoms, cyano moieties and azido moieties, or, where the poly(glycidyl azide) product is prepared from a product that is prepared by insertion of two or more moieties derived from epichlorohydrin into an ether molecule, R is a monovalent straight or branched chain alkyl radical having from 1 to 4 carbon atoms which may be substituted with atoms and moieties selected from the group consisting of hydrogen atoms, chlorine atoms, fluorine atoms, cyano moieties and azido moieties; and $R^1$ is a monovalent straight chain, branched or cyclic alkoxy radical, a monovalent oxyaryl radical or combination thereof, wherein said $R^1$ may be substituted with atoms and moieties selected from the group consisting of hydrogen atoms, chlorine atoms, fluorine atoms, cyano moieties and azido moieties, or $R^1$ may be an azido moiety.

2. The product of claim 1 having less than 44 weight percent nitrogen.

3. The product of claim 1 having less than about one equivalent of hydroxyl moieties per 30,000 grams of product.

4. The product of claim 1 where R is selected from the group consisting of —CH₃, —CH₂CH₃, —CH₂CH₂CH₃, —CH₂CH₂N₃, and —CH₂CH₂CH₂N₃ radicals.

5. The product of claim I where $R^1$ is selected from the group consisting of —OCH₃, —OCH₂CH₃, —OCH₂CH₂CH₃, —OCH₂CH₂N₃ and —OCH₂CH₂N₃ and —OCH₂C₆H₅ radicals.

6. A composition comprising oxidizer, binder prepolymer and the product of claim 1.

7. The product of claim 1 wherein said polymer is selected from the group consisting of CH₃OCH₂CH(CH₃)(OCH₂CH(CH₃)((OCH₂CH(CH₂N₃))ₙN₃, CH₃CH₂(OCH₂CH(CH₂N₃))ₙOCH₂CH₃, N₃CH₂CH₂(OCH₂CH(CH₂  N₃))ₙN₃, CH₃(OCH₂CH(CH₂N₃))ₙOCH₂CH₂N₃ and CH₃OCH₂CH₂(OCH₂ CH(CH₂N₃))ₙN₃, where in the above formulas, n is a number between 2 and 18.

8. The product of claim 1 having a number average molecular weight of 400 to 1000.

* * * * *

UNITED STATES PATENT AND TRADEMARK OFFICE
CERTIFICATE OF CORRECTION

PATENT NO. : 5,565,650
DATED : October 15, 1996
INVENTOR(S) : Birger Johannessen et al.

It is certified that error appears in the above-indentified patent and that said Letters Patent is hereby corrected as shown below:

On the title page, under "References Cited", "U.S. Patent Documents", add

-- 4,781,861   11/1988   Wilson et al.      260/349
   4,268,450   05/1981   Frankel et al.     260/349
   4,288,262   09/1981   Flanagan et al.    149/19.6
   4,379,894   04/1983   Frankel et al.     525/403
   4,486,351   12/1984   Earl               260/349
   4,146,736   03/1979   Scheffel et al.    568/607
   4,431,845   02/1984   Young et al.       568/606. --

On the title page, under "References Cited", add

-- Kern, R. J., Journal of Organic Chemistry, 33, (1960) pp. 388-390

Huber, W., "Titration in Nonaqueous Solvents," Academic Press, New York, NY (1967), p. 215 --

Col. 1, line 15, "moleties" should read -- moieties --.

Col. 1, line 22, "moleties" should read -- moieties --.

Col. 2, line 9, "moleties" should read -- moieties --.

UNITED STATES PATENT AND TRADEMARK OFFICE
CERTIFICATE OF CORRECTION

PATENT NO. : 5,565,650                     Page 2 of 4

DATED : October 15, 1996

INVENTOR(S) : Birger Johannessen et al.

It is certified that error appears in the above-indentified patent and that said Letters Patent is hereby corrected as shown below:

Col. 2, line 10, "moleties" should read -- moieties --.

Col. 2, line 11, "moleties" should read -- moieties --.

Col. 2, line 18, "moleties" should read -- moieties --.

Col. 2, line 19, "moleties" should read -- moieties --.

Col. 2, line 20, "moleties" should read -- moieties --.

Col. 2, line 22, "moleties" should read -- moieties -- (two occurrences).

Col. 2, line 42, "moleties" should read -- moieties --.

Col. 2, line 45, "moleties" should read -- moieties --.

Col. 2, line 49, "moleties" should read -- moieties --.

Col. 2, line 55, "moleties" should read -- moieties --.

Col. 2, line 67, "moleties" should read -- moieties -- (two occurrences).

Col. 3, line 2, "moleties" should read -- moieties --.

Col. 3, line 5, "moleties" should read -- moieties --.

Col. 3, line 22, delete the comma after the first subscript "n".

Col. 3, line 63, "moleties" should read -- moieties --.

Col. 3, line 64, "moleties" should read -- moieties --.

UNITED STATES PATENT AND TRADEMARK OFFICE
CERTIFICATE OF CORRECTION

PATENT NO. : 5,565,650

DATED : October 15, 1996

INVENTOR(S) : Birger Johannessen et al.

It is certified that error appears in the above-indentified patent and that said Letters Patent is hereby corrected as shown below:

Col. 3, line 65, "moleties" should read -- moieties --.

Col. 4, line 4, "moleties" should read -- moieties --.

Col. 4, line 47, "moleties" should read -- moieties --.

Col. 6, line 16, "1:1.0" should read -- 1:10 --.

Col. 7, line 33, "cooled 30°C" should read -- cooled to 30°C --.

Col. 8, line 58, replace the formula with

-- $CH_3OCH_2CH(CH_3)OCH_2CH(CH_3)(OCH_2CH(CH_2N_3))_nN_3$ --.

Col. 9, line 48, "5 tort" should read -- 5 torr --.

Col. 11, lines 4-5, "(0 023% water)" should read -- (0.023% water) --.

Col. 12, line 12, "18:" should read -- 18; --.

UNITED STATES PATENT AND TRADEMARK OFFICE
CERTIFICATE OF CORRECTION

PATENT NO. : 5,565,650
DATED : October 15, 1996
INVENTOR(S) : Birger Johannessen et al.

It is certified that error appears in the above-indentified patent and that said Letters Patent is hereby corrected as shown below:

Col. 12, line 23, "monovalent straight" should read -- monovalent, straight --.

Col. 12, line 33, "moleties" should read -- moieties --.

Signed and Sealed this

Fourteenth Day of October, 1997

Attest:

BRUCE LEHMAN

Attesting Officer

Commissioner of Patents and Trademarks